United States Patent

Hester, Jr.

[11] 3,994,941
[45] Nov. 30, 1976

[54] PREPARATION OF 1-(2-PHTHALIMIDOETHYL)-4H-s-TIAZOLO[4,3-a][1,4]BENZODIAZEPINES

[75] Inventor: Jackson B. Hester, Jr., Galesburg, Mich.

[73] Assignee: The Upjohn Company, Kalamazoo, Mich.

[22] Filed: Oct. 20, 1975

[21] Appl. No.: 623,973

[52] U.S. Cl. .................. 260/308 R; 260/295 T; 424/263; 424/269
[51] Int. Cl.² ...................................... C07D 487/04
[58] Field of Search .................. 260/308 R, 295 T

[56] References Cited
UNITED STATES PATENTS 3,842,090  10/1974  Gall et al. ............... 260/308 R
3,882,139  5/1975  Gall et al. ............... 260/308 R

*Primary Examiner*—Alton D. Rollins
*Attorney, Agent, or Firm*—Hans L. Berneis

[57] ABSTRACT

A process for the production of compounds of the formula III:

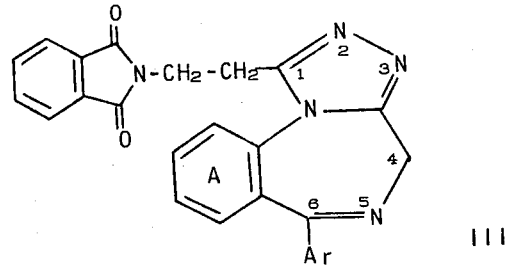

wherein ring A is unsubstituted or substituted by fluoro, chloro, bromo, trifluoromethyl, or nitro, and wherein Ar is phenyl, o-chlorophenyl, o-fluorophenyl, or 2-pyridyl, is claimed in which the starting compound is the corresponding 1-methyl-6-substituted-4H-s-triazolo[4,3-a][1,4]-benzodiazepine. Compound III is converted to compoud IV or V, the corresponding 1-(2-aminoethyl)-6-substituted-4H-s-triazolo[4,3-a][1,4]benzodiazepines, which are known antidepressant and anti-anxiety agents.

7 Claims, No Drawings

PREPARATION OF 1-(2-PHTHALIMIDOETHYL)-4H-S-TIAZOLO[4,3-A][1,4]BENZODIAZEPINES

BACKGROUND OF THE INVENTION

This invention is concerned with a process for the production of 1-[2-(phthalimidoethyl)]-6-substituted-4H-s-triazolo[4,3-a][1,4]benzodiazepines, which are intermediates for the production of 1-(2-aminoethyl)-6-substituted-4H-s-triazolo[4,3-a][1,4]benzodiazepines.

The novel process and the products thus produced can be illustratively represented as follows:

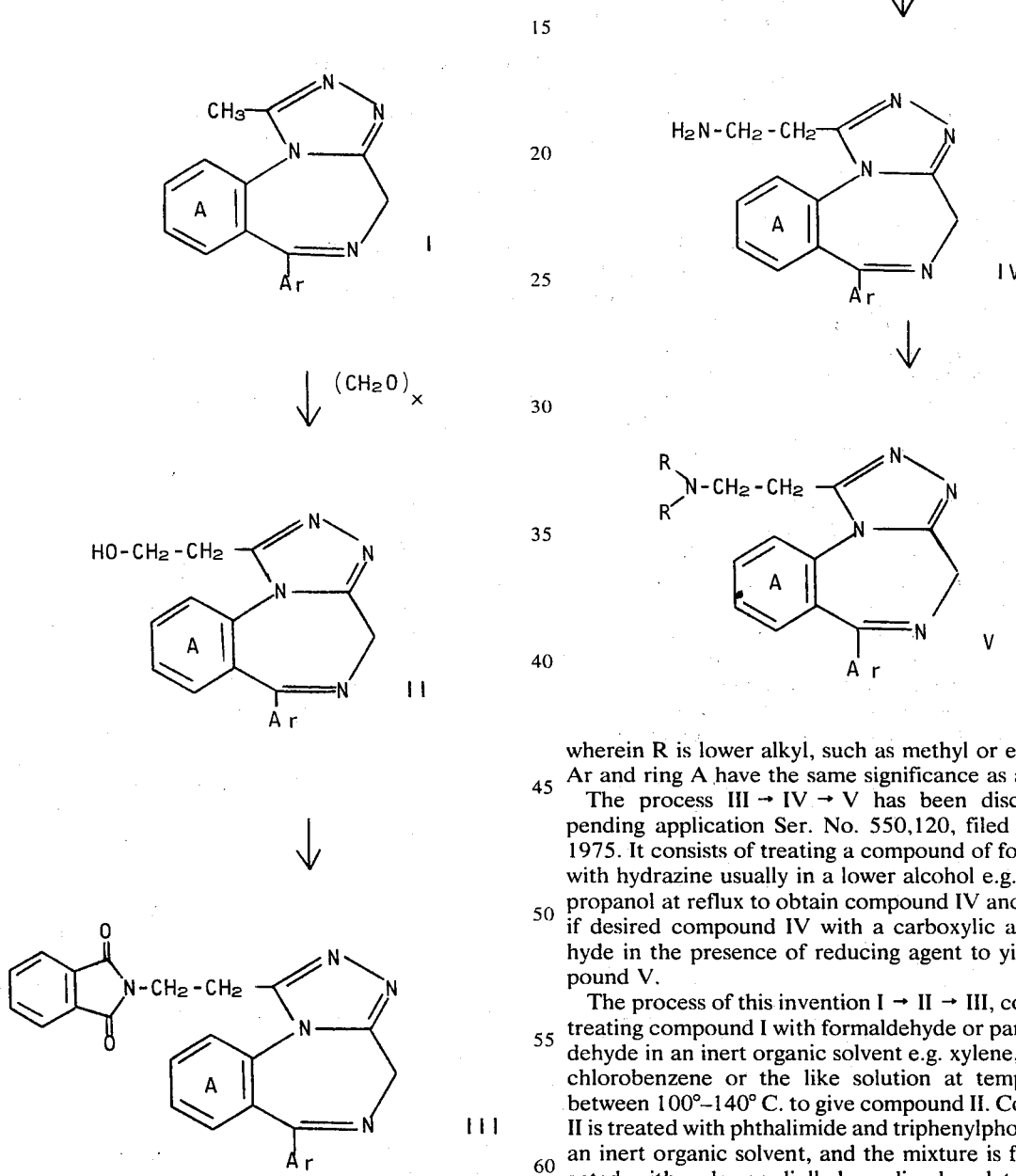

wherein Ar is phenyl, o-chlorophenyl, o-fluorophenyl, or 2-pyridyl; and wherein the A ring is unsubstituted or substituted by fluoro, chloro, bromo, trifluoromethyl, or nitro.

Compound III is converted to 1-(2-aminoethyl)-6-phenyl-4H-s-triazolo[4,3-a][1,4]benzodiazepines IV and V by the following process:

wherein R is lower alkyl, such as methyl or ethyl; and Ar and ring A have the same significance as above.

The process III → IV → V has been disclosed in pending application Ser. No. 550,120, filed Feb. 14, 1975. It consists of treating a compound of formula III with hydrazine usually in a lower alcohol e.g. ethanol, propanol at reflux to obtain compound IV and treating if desired compound IV with a carboxylic acid aldehyde in the presence of reducing agent to yield compound V.

The process of this invention I → II → III, comprises: treating compound I with formaldehyde or paraformaldehyde in an inert organic solvent e.g. xylene, toluene, chlorobenzene or the like solution at temperatures between 100°–140° C. to give compound II. Compound II is treated with phthalimide and triphenylphosphine in an inert organic solvent, and the mixture is finally reacted with a lower dialkyl azodicarboxylate to give compound III.

PREFERRED EMBODIMENT OF THE INVENTION

The preferred compounds of formula III which are subsequently converted to compounds IV and V are those having the substituent in ring A in the 8-position, and in particular those wherein said substituent is a halogen and wherein Ar is phenyl, o-chloro- or o-fluorophenyl.

The intermediate compounds of formula II have tranquilizing and sedative activity and can be used for this purpose in man in dosages from 1 to 15 mg. preferably from 2 to 10 mg. for single unit dosages. Compounds of formula II moreover can be used for the tranquilization of mammals, like cattle or zoo animals during travel in dosages of 0.2 to 2 mg./kg.; preferably using the low dosage range for animals over 25 kg.

The compounds of formula III of this application are useful as intermediates for the compounds of formula IV and V as will be described subsequently in examples.

The latter compounds IV and preferably the alkylated species compounds V are particularly useful as anti-depressant agents.

THE ANTI-DEPRESSANT ACTION:

The main function of an antidepressant is to return the depressed individual to normal function. This should be carefully differentiated from psychic stimulants such as the amphetamines which produce overstimulation in the normal individual.

Many different methods have been and are used to evaluate anti-depressant activity. In general these methods involve antagonism of a depressant such as reserpine or tetrabenazine or a synergistic increase of the toxicity of certain compounds (i.e., yohimbine or 3,4-dihydroxyphenylalanine) and comparison of the drug action of the new compound with other known anti-depressants. No single test alone can determine whether or not a new compound is an antidepressant or not, but the profile evidenced by various tests will establish the anti-depressant action if present. A number of such tests are described below.

Hypothermic tests with oxotremorine: [1-[4-(pyrrolidinyl)-2-butynyl]-2-pyrrolidinone].

Oxotremorine (as well as apomorphine and tetrabenazine) produces hypothermic responses in mice. This response is blocked by anticholinergics and anti-depressants such as atropine and imipramine.

Oxotremorine produces a very pronounced hypothermia which reaches a peak 60 minutes after administration.

At 0.6 mg./kg. the body temperature of a mouse is decreased about 13° F. (when the mouse is kept at room temperature). This temperature decrease is antagonized by anti-depressants e.g. desipramine, imipramine, doxepine, and others as can be seen from Table I.

TABLE 1

Effect of Various Compounds on Oxotremorine-Induced Hypothermia in Mice

| Compound | Dose mg./kg. I. P. | Absorption Time (min) | Body Temperature ° F.- Change From Vehicle Control After Minutes | | | |
|---|---|---|---|---|---|---|
| | | | 15 | 30 | 60 | 90 |
| Oxotremorine (Control) | 0.6 | | −5.8 | −11.6 | −13.2 | −8.0 |
| Desipramine | 25 | 30 | −3.5 | −3.5 | −4.1 | −3.6 |
| Imipramine | 25 | 30 | −0.4 | −3.3 | −5.6 | −6.4 |
| Iprindole | 25 | 30 | −6.3 | −11.8 | −12.8 | −11.9 |
| Doxepine | 25 | 30 | −2.3 | −7.1 | −11.0 | −12.3 |
| Amitriptyline | 25 | 30 | +0.7 | −2.4 | −5.4 | −6.8 |
| Amphetamine | 5 | 30 | −1.5 | −4.3 | −4.4 | −2.2 |

The compounds of formula V were tested as follows:

Four male mice of 18–22 g. (Strain CF=Carworth Farms) were injected intraperitoneally with 1 mg. of oxotremorine. The lowering of the body temperature was measured rectally with an electronic thermometer, before and 30 minutes after drug administration. After the drug administration the mice were kept at 19° C. in cages. A raise of 4 degrees Fahrenheit over the oxotremorine body temperature was taken as indicative of anti-depressant activity.

Potentiation of yohimbine aggregation toxicity: the $LD_{50}$ of yohimbine hydrochloride [YCl] in mice is 45 mg./kg. i.p. Administration of 30 mg./kg. of [YCl] was non-lethal. If an anti-depressant is administered prior to the [YCl] (30 mg./kg.), the lethality of the [YCl] is increased.

As a control ten male CF mice, 18–22 g., are injected with [YCl] (30 mg./kg) in saline solution. Groups of ten mice are injected with varying doses of the antidepressant 30 minutes before the administration of [YCl] (30 mg./kg.). After two hours the $LD_{50}$'s are determined. No mice or only one mouse is killed from 30 mg./kg. of [YCl]. In the presence of an anti-depressant an increase in the toxicity of [YCl] is found.

Potentiation of apomorphine gnawing: a group of 4 mice (male, CF, 18–22 g.) are administered the test compound intraperitoneally 1 hour prior to the subcutaneous injection of apomorphine hydrochloride 1 mg./kg. The mice are then placed in a plastic box (6 inches × 11 inches × 5 inches) lined at the bottom with a cellophane-backed, absorbent paper. The degree of damage to the paper at the end of 30 minutes is scored from zero to 4. The scores 3 and 4 indicated that the compound is a potentiator of apomorphine in this test.

In this testing system, 1-[2-(dimethylamino)ethyl]-8-chloro-6-phenyl-4H-s-triazolo[4,3-a][1,4]benzodiazepine bis (cyclohexanesulfamate) showed antidepressant activity.

The pharmaceutical forms of compound V including the preferred compounds V contemplated by this invention include pharmaceutical compositions suited for oral, parenteral, and rectal use, e.g., tablets, powder packets, cachets, dragees, capsules, solutions, suspensions, sterile injectable forms, suppositories, bougies, and the like. Suitable diluents or carriers such as carbohydrates (lactose), proteins, lipids, calcium phosphate, cornstarch, stearic acid, methylcellulose and the like may be used as carriers or for coating purposes. Water and oils, e.g. coconut oil, sesame oil, safflower oil, cottonseed oil, peanut oil may be used for preparing solutions or suspensions of the active drug. Sweetening, coloring, and flavoring agents may be added.

For mammals and birds food premixes, with starch, oatmeal, dried fishmeat, fishmeal, flour, and the like can be prepared.

As anti-depressants the compounds of formula V or salts thereof can be used in dosages of 1–50 mg./kg.

preferably 5–20 mg./kg. in oral or injectable preparations as described above, to alleviate anxiety and depression in mammals, including man. Larger mammals of more than 10 kg. body weight are tranquilized at the low dosages, whereas the small test animals need the higher dosages per kilogram.

The starting materials of formula I of this invention, substituted or unsubstituted 1-methyl-6-phenyl-4H-s-triazolo-[4,3-a][1,4]benzodiazepines, are known in the art, e.g. Hester et al., J. Med. Chem. 14, 1078 [1971]; and U.S. Pat. No. 3,734,922.

In carrying out the process of this invention a selected compound of formula I, preferably in an inert organic solvent with a boiling point over 100° C., is reacted with formaldehyde gas or a formaldehyde gas releasing agent, such as paraformaldehyde. As inert organic solvents the xylenes (ortho, meta, or para, or mixtures thereof), toluene, chlorobenzene, dichlorobenzenes (o-, m-, or p-), chlorotoluene (o-, m-, or p-) or the like, are usable. All of these solvents are inert with respect to the starting compound I and the reagent formaldehyde. The temperature of the reaction is kept between 100° to 140° C. or in a sealed vessel up to 160° C. The formaldehyde can be used as gas to bubble through the solution or can be added as paraformaldehyde. It is also possible to perform the reaction in a closed container like a sealed reaction vessel and thus use temperatures up to 160° C. and at the same time prevent loss of formaldehyde. The reaction period for this reaction preferably is between 4 to 36 hours and is not critical. After the reaction is terminated, the solvent is removed, usually by distillation, and the compound II is isolated by conventional procedures, e.g. extraction, chromatography, and crystallization.

The compound of formula II, thus, obtained is then dissolved in an inert organic solvent such as tetrahydrofuran, dioxane, ethers, e.g. diethyl ether, dibutyl ether, chloroform, or the like and treated with phthalimide and triphenylphosphine. These two reagents, phthalimide and triphenylphosphine, as well as the starting compound II for this reaction are used in about equal molar quantities with up to 10 to 15% excess for the reagents compared to compound II. In the preferred method the reaction is carried out between 0° to 50° C. in a nitrogen atmosphere. Thereafter a dialkyl (dimethyl, diethyl, dipropyl, or the like) azodicarboxylate is added in equal molar quantity as the two reagents above. The reaction is continued for 12 to 48 hours at between 15° to 50° C.; preferably with continuous stirring.

Thereafter the reaction mixture is concentrated and the remaining solids (compound III) are isolated and purified by standard procedures such as extraction, crystallization and chromatography.

The following examples are illustrative of the process of the present invention, but are not to be construed as limiting.

EXAMPLE 1

8-Chloro-1-(2-hydroxyethyl)-6-phenyl-4H-s-triazolo[4,3-a][1,4]benzodiazepine.

A stirred mixture of 8-chloro-6-phenyl-1-methyl-4H-s-triazolo[4,3-a][1,4]benzodiazepine (3.09 g., 0.01 mole) and paraformaldehyde (3 g.) in xylene (100 ml.) is warmed in an oil bath at 122°–124.5° C. At this temperature the starting material dissolved and the paraformaldehyde disproportionated to give gaseous formaldehyde which bubbled from the mixture. In this manner the insoluble paraformaldehyde is consumed in 30–60 minutes. Additional paraformaldehyde is therefore added to the mixture after 40 minutes (1 g.), 75 minutes (3 g.), 2 hours (3 g.), 3 hours (3 g.) and 4 hours (3 g.). After a total of 6 hours, the mixture is cooled and concentrated in vacuo. Residual xylene is removed by the addition of toluene and concentration of the mixture. The residue is dissolved in chloroform, filtered and chromatographed on silica gel (200 g.) with 3% methanol-97% chloroform. The unreacted starting material is eluted from the column first and crystallized from methanol-ethyl acetate to give 1.562 g. of 8-chloro-6-phenyl-1-methyl-4H-s-triazolo[4,3-a][1,4]-benzodiazepine of melting point 229.5°–230.5° C. The second compound eluted from the column is a by-product and the third compound is 8-chloro-1-(2-hydroxyethyl)-6-phenyl-4H-s-triazolo[4,3-a][1,4]benzodiazepine which is crystallized from methanol-ethyl acetate to give in three crops: 0.483 g., melting point 237°–238° C., 0.257 g., melting point 236.5°–237° C., and 0.129 g., melting point 235.5°–236.5° C. of 8-chloro-1-(2-hydroxyethyl)-6-phenyl-4H-s-triazolo[4,3-a][1,4]benzodiazepine. The analytical sample has a melting point 234°–236° C.

Anal. calcd. for $C_{18}H_{15}ClN_4O$:
  C, 63.83; H, 4.46; Cl, 10.47; N, 16.54.
Found: C, 63.87; H, 4.43; Cl, 10.53; N, 16.65.

EXAMPLE 2

8-Chloro-1-(2-phthalimidoethyl)-6-phenyl-4H-s-triazolo[4,3-a][1,4]benzodiazepine and its ethyl acetate solvent.

A stirred mixture of 8-chloro-6-phenyl-1-(2-hydroxyethyl)-4H-s-triazolo[4,3-a][1,4]benzodiazepine (0.677 g., 0.002 mole), phthalimide (0.324 g., 0.0022 mole), triphenylphosphine (0.576 g., 0.0022 mole) and dry tetrahydrofuran (20 ml.), under nitrogen, is treated with diethyl azodicarboxylate (0.383 g., 0.0022 mole) and stirred at ambient temperature (22°–25° C.) for 24 hours. The mixture is concentrated in vacuo and the residue chromatographed on silica gel (50 g.) with 3% methanol-97% chloroform. The product thus obtained is crystallized from ethyl acetate to give 8-chloro-1-(2-phthalimidoethyl)-6-phenyl-4H-s-triazolo[4,3-a][1,4]benzodiazepine ethyl acetate solvate of melting point 223.5°–226° C.

This product is kept in a vacuum dessicator at 12–18 mmHg pressure and 100° C. (steam bath) during 48 hours to give nonsolvated 8-chloro-1-(2-phthalimidoethyl)-6-phenyl-4H-s-triazolo[4,3-a][1,4]benzodiazepine.

EXAMPLE 3

8-Chloro-1-(2-hydroxyethyl)-6-(o-chlorophenyl)-4H-s-triazolo[4,3-a][1,4]benzodiazepine.

In the manner given in Example 1, 8-chloro-6-(o-chlorophenyl)-1-methyl-4H-s-triazolo[4,3-a][1,4]benzodiazepine in xylene is heated in an oil bath at 122°–124° C. with repeated addition of portions of paraformaldehyde to give 8-chloro-1-(2-hydroxyethyl)-6-(o-chlorophenyl)-4H-s-triazolo[4,3-a][1,4]benzodiazepine.

EXAMPLE 4

8-Chloro-1-(2-phthalimidoethyl)-6-(o-chlorophenyl)-4H-s-triazolo[4,3-a][1,4]benzodiazepine.

In the manner given in Example 2, 8-chloro-1-(2-hydroxyethyl)-6-(o-chlorophenyl)-4H-s-triazolo[4,3-a]-[1,4]benzodiazepine in dioxane is treated with phthalimide, triphenylphosphine and subsequently with diethyl azodicarboxylate to give 8-chloro-1-(2-phthalimidoethyl)-6-(o-chlorophenyl)-4H-s-triazolo[4,3-a][1,4]benzodiazepine.

EXAMPLE 5

8-Chloro-1-(2-hydroxyethyl)-6-(2-pyridyl)-4H-s-triazolo[4,3-a][1,4]benzodiazepine.

In the manner given in Example 1, 8-chloro-methyl-6-(2-pyridyl)-4H-s-triazolo[4,3-a][1,4]benzodiazepine in xylene is heated in an oil bath with repeated additions of portions of paraformaldehyde to give 8-chloro-1-(2-hydroxyethyl)-6-(2-pyridyl)-4H-s-triazolo-[4,3-a][1,4]benzodiazepine.

EXAMPLE 6

8-Chloro-1-(2-phthalimidoethyl)-6-(2-pyridyl)-4H-s-triazolo[4,3-a][1,4]benzodiazepine.

In the manner given in Example 2, 8-chloro-1-(2-hydroxyethyl)-6-(2-pyridyl)-4H-s-triazolo[4,3-a][1,4]-benzodiazepine in dioxane is treated with phthalimide, triphenylphosphine and subsequently with diethyl azodicarboxylate to give 8-chloro-1-(2-phthalimidoethyl)-6-(2-pyridyl)-4H-s-triazolo[4,3-a][1,4]benzodiazepine.

EXAMPLE 7

8-Fluoro-1-(2-hydroxyethyl)-6-phenyl-4H-s-triazolo[4,3-a][1,4]benzodiazepine.

In the manner given in Example 1, 8-fluoro-1-methyl-6-phenyl-4H-s-triazolo[4,3-a][1,4]benzodiazepine in xylene is heated in an oil bath with repeated additions of portions of paraformaldehyde to give 8-fluoro-1-(2-hydroxyethyl)-6-phenyl-4H-s-triazolo[4,3-a][1,4]benzodiazepine.

EXAMPLE 8

8-Fluoro-1-(2-phthalimidoethyl)-6-phenyl-4H-s-triazolo[4,3-a][1,4]benzodiazepine.

In the manner given in Example 2, 8-fluoro-1-(2-hydroxyethyl)-6-phenyl-4H-s-triazolo[4,3-a][1,4]benzodiazepine in dioxane is treated with phthalimide, triphenylphosphine and subsequently with dimethyl azodicarboxylate to give 8-fluoro-1-(2-phthalimidoethyl)-6-phenyl-4H-s-triazolo[4,3-a][1,4]benzodiazepine.

EXAMPLE 9

8-Chloro-1-(2-hydroxyethyl)-6-(o-fluorophenyl)-4H-s-triazolo[4,3-a][1,4]benzodiazepine.

In the manner given in Example 1, 8-chloro-6-(o-fluorophenyl)-1-methyl-4H-s-triazolo[4,3-a]1,4]benzodiazepine in xylene is heated in an oil bath with repeated additions of paraformaldehyde to give 8-chloro-1-(2-hydroxyethyl)-6-(o-fluorophenyl)-4H-s-triazolo[4,3-a]-[1,4]benzodiazepine.

EXAMPLE 10

8-Chloro-1-(2-phthalamidoethyl)-6-(o-fluorophenyl)-4H-s-triazolo[4,3-a][1,4]benzodiazepine.

In the manner give in Example 2, 8-chloro-1-(2-hydroxyethyl)-6-(o-fluorophenyl)-4H-s-triazolo[4,3-a]-[1,4]benzodiazepine in dioxane is treated with phthalimide, triphenylphosphine and subsequently with diethyl azodicarboxylate to give 8-chloro-1-(2-phthalimidoethyl)-6-(o-fluorophenyl)-4H-s-triazolo[4,3-a][1,4]benzodiazepine.

EXAMPLE 11

8-Bromo-1-(2-hydroxyethyl)-6-(2-pyridyl)-4H-s-triazolo[4,3-a][1,4]benzodiazepine.

In the manner given in Example 1, 8bromo-1-methyl-6-(2-pyridyl)-4H-s-triazolo[4,3-a][1,4]benzodiazepine in xylene is heated in an oil bath at 105°–110° C. with formaldehyde gas bubbling through the solution to give 8-bromo-1-(2-hydroxyethyl)-6-(2-pyridyl)-4H-s-triazolo-[4,3-a][1,4]benzodiazepine.

EXAMPLE 12

8-Bromo-1-(2-phthalimidoethyl)-6-(2-pyridyl)-4H-s-triazolo[4,3-a][1,4]benzodiazepine.

In the manner given in Example 2, 8-bromo-1-(2-hydroxyethyl)-6-(2-pyridyl)-4H-s-triazolo[4,3-a][1,4]-benzodiazepine in dioxane is treated with phthalimide, triphenylphosphine and subsequently with dipropyl azodicarboxylate to give 8-bromo-1-(2-phthalimodethyl)-6-(2-pyridyl)-4H-s-triazolo[4,3-a][1,4]benzodiazepine.

EXAMPLE 13

8Nitro-1-(2-hydroxyethyl)-6-(o-chlorophenyl)-4H-s-triazolo[4,3-a][1,4]benzodiazepine.

In the manner given in Example 1, 8-nitro-6-(o-chlorophenyl)-1-methyl-4H-s-triazolo[4,3-a][1,4]-benzodiazepine in xylene was heated in an oil bath with repeated additions of portions of paraformaldehyde to give 8-nitro-1-(2-hydroxyethyl)-6-(o-chlorophenyl)-4H-s-triazolo[4,3-a][1,4]benzodiazepine.

EXAMPLE 14

8-Nitro-1-(2-phthalimidoethyl)-6-(o-chlorophenyl)-4H-s-triazolo[4,3-a][1,4]benzodiazepine.

In the manner given in Example 2, 8-nitro-1-(2-hydroxyethyl)-6-(o-chlorophenyl)-4H-s-triazolo[4,3-a]-[1,4]benzodiazepine in dioxane is treated with phthalimide, triphenylphosphine and subsequently with diethyl azodicarboxylate to give 8-nitro-1-(2-phthalimidoethyl)-6-(o-chlorophenyl)-4H-s-triazolo[4,3-a][1,4]benzodiazepine.

EXAMPLE 15

8-Trifluoromethyl-1-(2-hydroxyethyl)-6-(o-chlorophenyl)-4H-s-triazolo[4,3-a][1,4]benzodiazepine.

In the manner given in Example 1, 8-trifluoromethyl-6-(o-chlorophenyl)-1-methyl-4H-s-triazolo[4,3-a][1,4]-benzodiazepine in xylene is heated with excess paraformaldehyde in a sealed, glass-lined vessel at 155°–160° C. to give 8-trifluoromethyl-1-(2-hydroxyethyl)-6-(o-chlorophenyl)-4H-s-triazolo[4,3-a][1,4]benzodiazepine.

EXAMPLE 16

8-Trifluoromethyl-1-(2-phthalimidoethyl)-6-phenyl-4H-s-triazolo[4,3-a][1,4]benzodiazepine.

In the manner given in Example 2, 8-trifluoromethyl-1-(2-hydroxyethyl)-6-(o-chlorophenyl)-4H-s-triazolo-[4,3-a][1,4]benzodiazepine in dioxane is treated with dimethyl azodicarboxylate to give 8-trifluoromethyl-1-

(2-phthalimidoethyl)-6-(o-chlorophenyl)-4H-s-triazolo[4,3-a][1,4]benzodiazepine.

EXAMPLE 17

1-(2-Hydroxyethyl)-6-(o-chlorophenyl)-4H-s-triazolo[4,3-a][1,4]benzodiazepine.

In the manner given in Example 1, 6-(o-chlorophenyl)-1-methyl-4H-s-triazolo[4,3-a][1,4]benzodiazepine in xylene is heated with repeated additions of paraformaldehyde in an oil bath to give 1-(2-hydroxyethyl)-6-(o-chlorophenyl)-4H-s-triazolo[4,3-a][1,4]benzodiazepine.

EXAMPLE 18

1-(2-phthalimidoethyl)-6-(o-chlorophenyl)-4H-s-triazolo[4,3-a][1,4]benzodiazepine.

In the manner given in Example 2, 1-(2-hydroxyethyl)-6-(o-chlorophenyl)-4H-s-triazolo[4,3-a][1,4]benzodiazepine in dioxane is treated with phthalimide, triphenylphosphine and subsequently with diethyl azodicarboxylate to give 1-(2-phthalimidoethyl)-6-(o-chlorophenyl)-4H-s-triazolo-[4,3-a][1,4]benzodiazepine.

EXAMPLE 19

8-Bromo-1-(2-hydroxyethyl)-6-phenyl-4H-s-triazolo[4,3-a][1,4]benzodiazepine.

In the manner given in Example 1, 8-bromo-1-methyl-6-phenyl-4H-s-triazolo[4,3-a][1,4]benzodiazepine in xylene is heated in an oil bath with repeated additions of portions of paraformaldehyde to give 8-bromo-1-(2-hydroxyethyl)-6-phenyl-4H-s-triazolo[4,3-a][1,4]benzodiazepine.

EXAMPLE 20

8-Bromo-1-(2-phthalimidoethyl)-6-phenyl-4H-s-triazolo[4,3-a][1,4]benzodiazepine.

In the manner given in Example 2, 8-bromo-1-(2-hydroxyethyl)-6-phenyl-4H-s-triazolo[4,3-a][1,4]benzodiazepine in dioxane is treated with phthalimide, triphenylphosphine and subsequently with diethyl azodicarboxylate to give 8-bromo-1-(2-phthalimidoethyl)-6-phenyl-4H-s-triazolo[4,3-a][1,4]benzodiazepine.

In the manner given in the prior Examples other 1-(2-phthalimidoethyl)-6-substituted-4H-s-triazolo[4,3-a]-[1,4]benzodiazepines can be synthesized. Representative compounds thus obtained include: 8-fluoro-1-(2-phthalimidoethyl)-6-(o-chlorophenyl)-4H-s-triazolo[4,3-a][1,4]benzodiazepine; 8-fluoro-1-(2-phthalimidoethyl)-6-(o-fluorophenyl)-4H-s-triazolo[4,3-a][1,4]benzodiazepine; 8-bromo-1-(2-phthalimidoethyl)-6-(o-chlorophenyl)-4H-s-triazolo[4,3-a][1,4]benzodiazepine; 8-nitro-1-(2-phthalimidoethyl)-6-phenyl-4H-s-triazolo[4,3-a][1,4]benzodiazepine; 8-nitro-1-(2-phthalimidoethyl)-6-(o-fluorophenyl)-4H-s-triazolo[4,3-a][1,4]benzodiazepine; 8-trifluoromethyl-1-(2-phthalimidoethyl)-6-(o-chlorophenyl)-4H-s-triazolo[4,3-a][1,4]benzodiazepine; 8-trifluoromethyl-1-(2-phthalimidoethyl)-6-(o-fluorophenyl)-4H-s-triazolo[4,3-a][1,4]benzodiazepine; 7-chloro-1-(2-phthalimidoethyl)-6-(o-chlorophenyl)-4H-s-triazolo[4,3-a][1,4]benzodiazepine; 9-chloro-1-(2-phthalimidoethyl)-6-phenyl-4H-s-triazolo-[4,3-a][1,4]benzodiazepine; 10-chloro-1-(2-phthalimidoethyl)-6-phenyl-4H-s-triazolo[4,3-a][1,4]benzodiazepine; 9-chloro-1-(2-phthalimidoethyl)-6-(o-fluorophenyl)-4H-s-triazolo[4,3-a][1,4]benzodiazepine; 9-bromo-1-(2-phthalimidoethyl)-6-(o-chlorophenyl)-4H-s-triazolo[4,3-a][1,4]benzodiazepine; 10-trifluoromethyl-1-(2-phthalimidoethyl)-6-(o-chlorophenyl)-4H-s-triazolo[4,3-a][1,4]benzodiazepine; 8-chloro-1-(2-phthalimidoethyl)-6-(m-chlorophenyl)-4H-s-triazolo[4,3-a][1,4]benzodiazepine; 8-chloro-1-(2-phthalimidoethyl)-6-(p-chlorophenyl)-4H-s-triazolo[4,3-a][1,4]benzodiazepine; 8-nitro-1-(2-phthalimidoethyl)-6-(2-pyridyl)-4H-s-triazolo[4,3-a][1,4]benzodiazepine; 8-trifluoromethyl-1-(2-phthalimidoethyl)-6-(2-pyridyl)-4H-s-triazolo[4,3-a][1,4]benzodiazepine; 8-fluoro-1-(2-phthalimidoethyl)-6-(2-pyridyl)-4H-s-triazolo[4,3-a][1,4]benzodiazepine; 9-chloro-1-(2-phthalimidoethyl)-6-(2-pyridyl)-4H-s-triazolo[4,3-a][1,4]benzodiazepine; 10-chloro-1-(2-phthalimidoethyl)-6-(2-pyridyl)-4H-s-triazolo[4,3-a][1,4]benzodiazepine; 10-trifluoromethyl-1-(2-phthalimidoethyl)-6-(2-pyridyl)-4H-s-triazolo[4,3-a][1,4]benzodiazepine; 7-bromo-1-(2-phthalimidoethyl)-6-(2-pyridyl)-4H-s-triazolo[4,3-a][1,4]benzodiazepine; and the like.

EXAMPLE 21

1-(2-Aminoethyl)-8-chloro-6-phenyl-4H-s-triazolo[4,3-a][1,4]benzodiazepine.

A stirred mixture of 8-chloro-6-phenyl-1-(2-phthalimidoethyl)-4H-s-triazolo[4,3-a][1,4]benzodiazepine, ethyl acetate solvate (37.6 g., 0.0675 mole) and absolute ethanol (340 ml.) is treated with hydrazine hydrate (7.43 g.) and warmed, under nitrogen, in an oil bath to 75° during 65 minutes, the bath is kept at this temperature for an additional 55 minutes. The mixture is then cooled in an ice bath, and the solid is collected by filtration and washed with absolute ethanol and methylene chloride. The combined filtrate is mixed with ice cold salt water and extracted with methylene chloride. The extract is washed with water, dried over anhydrous sodium sulfate and concentrated in vacuo. The residue is chromatographed on silica gel (1 kg.) with methanol and the resulting product is crystallized from methylene chloride diethyl ether to give 1-(2-aminoethyl)-8-chloro-6-phenyl-4H-s-triazolo-[4,3-a][1,4]benzodiazepine in 2 crops: 5.29 g. of melting point 198°–200° C. dec., and 2.37 g., of melting point 194°–196.5° C. dec. The analytical sample is crystallized from methanol-ethyl acetate and has a melting point of 205°–207° C.

EXAMPLE 22

1-[2-(Dimethylamino)ethyl]-8-chloro-6-phenyl-4H-s-triazolo[4,3-a][1,4]benzodiazepine bis (cyclohexanesulfamate).

A stirred mixture of 1-(2-aminoethyl)-8-chloro-6-phenyl-4H-s-triazolo[4,3-a][1,4]benzodiazepine (1.69 g., 0.005 mole) and acetonitrile (30 ml.) is treated successively with 37% aqueous formaldehyde (2 ml.) and acetic acid (0.29 ml.) and cooled in an ice bath. To this mixture is added sodium cyanoborohydride (500 mg., 0.008 mole) and the resulting mixture is kept under nitrogen, in the ice bath for 35 minutes and at ambient temperature for two hours 10 minutes. Acetic acid (4 drops) is added during the latter period to maintain a pH of about 7. The mixture is poured into cold water: the solution is saturated with sodium chloride and extracted with chloroform. The extract is washed with brine, dried over anhydrous sodium sulfate and concentrated. The residue is mixed with methanol (35 ml.) and 25% aqueous ethylenediamine (20 ml.) and refluxed under nitrogen for 70 minutes. The mixture is mixed with cold water, concentrated to remove methanol, saturated with sodium chloride and extracted with chloroform. The extract was washed with brine, dried over anhydrous sodium and concentrated. The residue is chromatographed on silica gel (100 g.) with methanol to give 1.20 g. of 1-[2-(dimethylamino)ethyl]-8-chloro-6-phenyl-4H-s-triazolo-[4,3-a][1,4]benzodiazepine as an oil. A solution of this oil in ethyl acetate is treated with an equal weight (1.2 g.) of cyclohexane-sulfamic acid in methanol and the resulting salt is crystallized to give 2.16 g. of 1-[2-(dimethylamino)-ethyl]-8-chloro-6-phenyl-4H-s-triazolo[4,3-a][1,4]benzodiazepine bis (cyclohexanesulfamate). The analytical sample is prepared by recrystallizing some of this material from ethanol-ethyl acetate and has a melting point of 132°–139° C.

Anal. calcd. for $C_{32}H_{46}ClN_7O_6S_2$:
C, 53.06; H, 6.40; Cl, 4.89; N, 13.54; S, 8.85.
Found: C, 52.73; H, 6.70; Cl, 4.61; N, 13.31; S, 8.84.

EXAMPLE 23

1-(2-Aminoethyl)-8-chloro-6-(o-chlorophenyl)-4H-s-triazolo[4,3-a][1,4]benzodiazepine.

In the manner given in Example 21, a mixture of 8-chloro-6-(o-chlorophenyl)-1-(2-phthalimidoethyl)-4H-s-triazolo[4,3-a][1,4]benzodiazepine is heated with hydrazine hydrate to give 1-(2-aminoethyl)-8-chloro-6-(o-chlorophenyl)-4H-s-triazolo[4,3-a][1,4]benzodiazepine.

EXAMPLE 24

1-[2-(Dimethylamino)ethyl]-8-chloro-6-(o-chlorophenyl)-4H-s-triazolo[4,3-a][1,4]benzodiazepine.

In the manner given in Example 22, a mixture of 1-(2-aminoethyl)-8-chloro-6-(o-chlorophenyl)-4H-s-triazolo[4,3-a][1,4]benzodiazepine, 37% aqueous formaldehyde and acetic acid in acetonitrile is treated with sodium cyanoborohydride and the resulting boron complex is warmed with aqueous ethylenediamine to give 1-[2-(dimethylamino)ethyl]-8-chloro-6-(o-chlorophenyl)-4H-s-triazolo[4,3-a][1,4]benzodiazepine.

EXAMPLE 25

1-(2-Aminoethyl)-8-fluoro-6-phenyl-4H-s-triazolo[4,3-a][1,4]benzodiazepine.

In the manner given in Example 21, a solution of 8-fluoro-6-phenyl-1-(2-phthalimidoethyl)-4H-s-triazolo-[4,3-a][1,4]benzodiazepine in ethanol is heated with hydrazine hydrate to give 1-(2-aminoethyl)-8-fluoro-6-phenyl-4H-s-triazolo[4,3-a][1,4]benzodiazepine.

EXAMPLE 26

1-[2-[(Dimethylamino)ethyl]-8-fluoro-6-phenyl-4H-s-triazolo[4,3-a][1,4]benzodiazepine.

In the manner given in Example 22, 1-(2-aminoethyl)-8-fluoro-6-phenyl-4H-s-triazolo[4,3-a][1,4]benzodiazepine in acetonitrile is treated with 37% aqueous formaldehyde and acetic acid and thereafter with sodium cyanoborohydride and the resulting boron complex is warmed with aqueous ethylenediamine to give 1-[2-[(dimethylamino)-ethyl]-8-fluoro-6-phenyl-4H-s-triazolo[4,3-a][1,4]benzodiazepine.

In the manner given in the preceding Examples, other compounds of formula V can be produced such as: 1-[2-(dimethylamino)ethyl]-6-(o-nitrophenyl)-8-trifluoromethyl-4H-s-triazolo[4,3-a][1,4]benzodiazepine; 1-(2-aminoethyl)-6-(m-bromophenyl)-7-ethoxy-4H-s-triazolo[4,3-a][1,4]benzodiazepine; 8-chloro-1-[2-(dimethylamino)ethyl]-6-(o-fluorophenyl)-4H-s-triazolo[4,3-a][1,4]benzodiazepine; 8-chloro-1-[2-(diethylamino)ethyl]-6-(2-pyridyl)-4H-s-triazolo[4,3-a][1,4]benzodiazepine; 1-[2-(dimethylamino)ethyl]-6-(chlorophenyl)-8-nitro-4H-s-triazolo[4,3-a][1,4]benzodiazepine; 8-trifluoromethyl-1-[(2-dimethylamino)ethyl]-6-phenyl-4H-s-triazolo[4,3-a][1,4]benzodiazepine; and the like.

I claim:
1. A process for the production of compounds of the formula III:

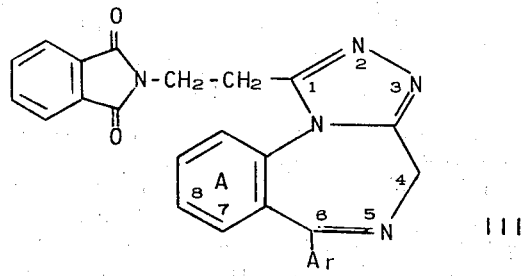

wherein ring A is unsubstituted or substituted by fluoro, chloro, bromo, trifluoromethyl, or nitro; and wherein Ar is phenyl, o-chlorophenyl, o-fluorophenyl, or 2-pyridyl, which comprises: reacting a compound of the formula I:

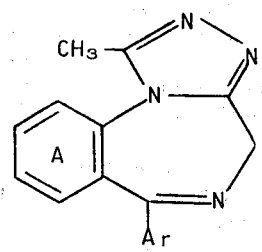

wherein A and Ar have the significance of above, at a temperature of 100°–160° C. with formaldehyde gas or a formaldehyde gas releasing agent to give a compound of the formula II:

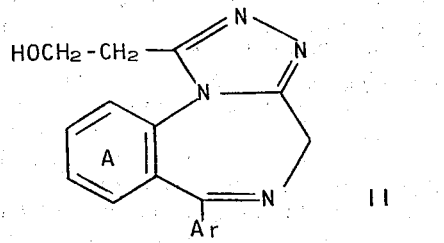

wherein the ring A and the group Ar are defined as above; and reacting compound II with phthalimide and triphenylphosphine followed by a dialkyl azodicarboxylate at 0° to 50° C. to produce the corresponding compound III of above.

2. The process of claim 1, wherein the starting material I is substituted in the 8-position.

3. The process of claim 1, wherein the formaldehyde gas releasing agent is paraformaldehyde at a temperature between 100°–140° C.

4. The process of claim 1, wherein the dialkyl azodicarboxylate is diethyl azodicarboxylate.

5. A process according to claim 1, for the preparation of 8-chloro-1-(2-phthalimidoethyl)-6-phenyl-4H-s-triazolo-[4,3-a][1,4]benzodiazepine which comprises:

1. heating 8-chloro-6-phenyl-1-methyl-4H-s-triazolo-[4,3-a][1,4]benzodiazepine in an inert organic solvent with paraformaldehyde to 100°–140° C. to give 8-chloro-1-(2-hydroxyethyl)-6-phenyl-4H-s-triazolo[4,3-a][1,4]benzodiazepine; and 2. treating this compound at 0° to 50° C. with phthalimide, triphenylphosphine and thereafter with a dialkyl azodicarboxylate.

6. The process of claim 5, wherein the inert organic solvent in step 1 is a mixture of xylenes.

7. The process of claim 5, wherein the dialkyl azodicarboxylate used in step 2 is diethyl azodicarboxylate.

* * * * *